United States Patent [19]
Adler et al.

[11] Patent Number: 5,911,722
[45] Date of Patent: Jun. 15, 1999

[54] LEBAN/GORDON SURGICAL HAND DRIVER

[75] Inventors: Jonathan Adler, Upper Brookville; Stanley Leban, New York; Gregg Gordon, Katonah, all of N.Y.

[73] Assignee: Millenium Devices LLC, Islandia, N.Y.

[21] Appl. No.: 09/120,470

[22] Filed: Jul. 23, 1998

[51] Int. Cl.⁶ .................................................. A61B 17/56
[52] U.S. Cl. ............................ 606/80; 606/104; 174/170
[58] Field of Search ................................. 606/80, 79, 85, 606/104, 180; 408/199, 210, 227; 81/57.39; 74/89, 89.15; 174/170

[56] References Cited

U.S. PATENT DOCUMENTS 4,249,617  2/1981  Cox, Jr. .................................... 173/170
4,524,650  6/1985  Marks .................................... 81/57.39

*Primary Examiner*—Guy V. Tucker
*Attorney, Agent, or Firm*—Charles I. Brodsky

[57] ABSTRACT

A surgical hand drill for inserting orthopedic screws and for drilling holes in the fixing of fractures and bone grafts employing a pair of bushings at opposite ends of a double-helix spiral drive shaft to maintain concentricity of rotation when transferring a squeeze hand motion to a pistol grip handle to a rotating drive motion for the screw and for the twist drill, with a compression-type return spring to return the drive shaft to its quiescent position, while providing a tactile feel to the surgeon as to the success in setting the screw into the bone, or drilling a hole, and which includes a quick disconnect adapter for accepting orthopedic screw driver tips of square, hexagonal and/or cross-fit end shank or other configurations, or twist drills.

8 Claims, 1 Drawing Sheet

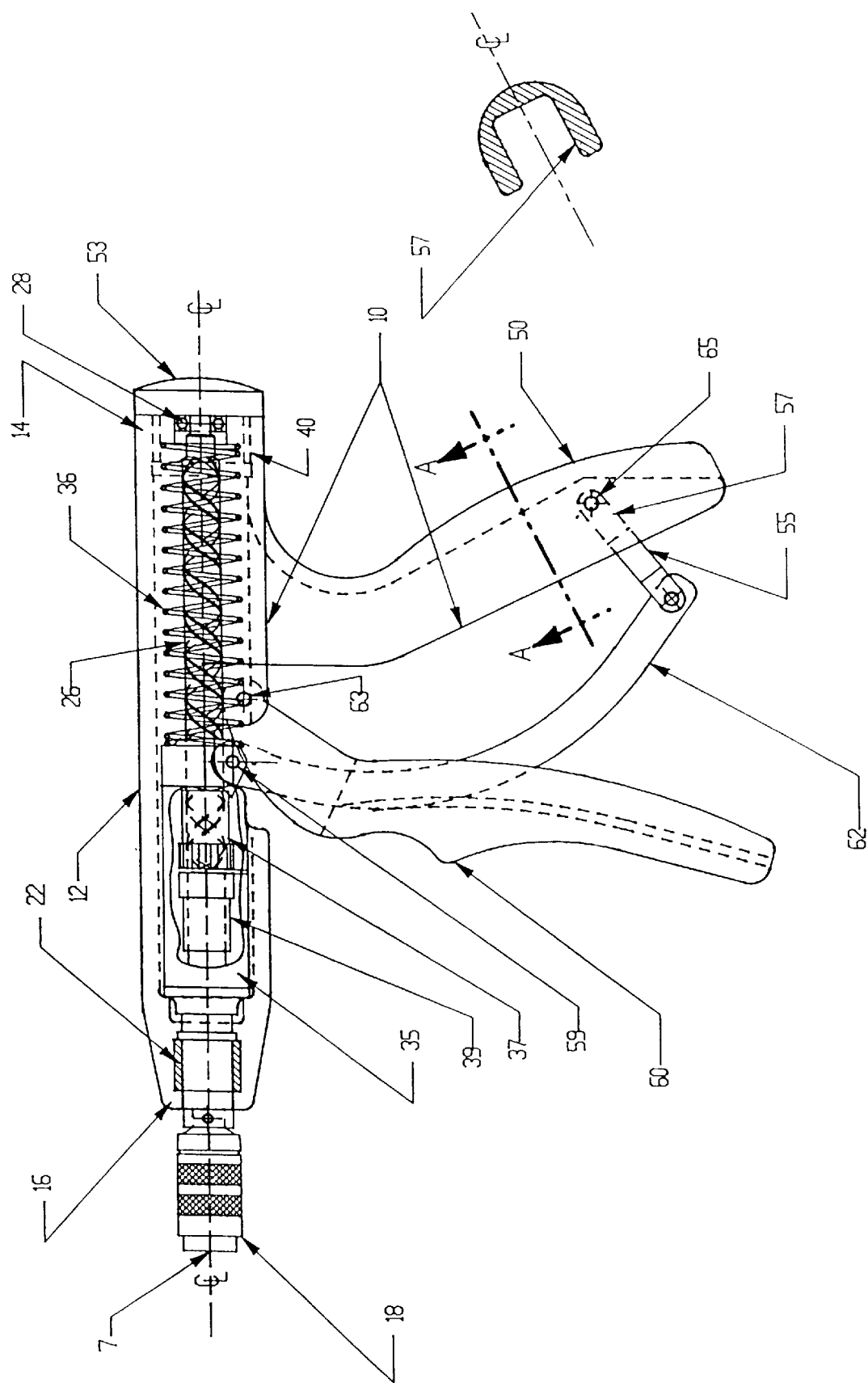

LEBAN/GORDON SURGICAL HAND DRIVER

FIELD OF THE INVENTION

This invention relates to manual drills useful in the medical profession, in general, and to a manual drill adapted for use by a surgeon in the fixing of fractures and bone grafts, and for drilling holes into bone, in particular.

BACKGROUND OF THE INVENTION

As is known and appreciated, the insertion of orthopedic screws or drilling of holes by a surgeon in peri-orbital, peri-cranial and other small bone applications typically entails the use of a non-powered, manually driven device. As is also known and understood, such insertions, whether it be for reducing fractures or for stabilizing fractures, customarily involves the surgeon—to insert the orthopedic screw, utilizing both hands—and at least one other person—to retract the wound area. Obviously, a savings in cost could result if the procedure could be accomplished by the surgeon acting alone, a savings in time could result where the surgeon did not have to communicate his or her instructions to that nurse or other person, a reduction in possible confusion could follow from eliminating the possibility of misinterpreting those instructions, and a savings in occupied space in the operating room could be had. If, at the same time, such a device could be designed ergonomic for comfortable and easy handling, with high degrees of tolerance for use at the exposed facial, or cranial, or other bones, and to be both sterilizable and autoclavable, a surgical device of such type would be highly desirable.

Recognizing that in use, the surgeon could then use one hand to retract the wound, and the other to hold the instrument in fashion to permit the driving of these orthopedic screws, or the drilling of holes into bone, it was realized that an essential feature of the instrument would have to be an ability to transfer a motion from the hand to a rotating motion for driving the screw into the bone. This led to an analysis of various squeeze-ratchet type assemblies, wherein the actuating of a pistol grip handle could produce a rotary torque for a 4 mm, 5 mm or similar orthopedic screw employed or to a mounted twist drill. Investigation led to possible devices for use, of a type set forth in U.S. Pat. Nos. 4,249,617 to Cox and 4,524,650 to Marks. Putting aside the fact that their disclosures were of assemblies that could rotate the screw in a direction to loosen it, as well as to tighten it (something which is not of significance in the surgical use intended for the present invention), there also came an appreciation that those devices allowed for a great deal of "wobble" and instability in the rotary motion imparted—something which could not be tolerated where only micro-movement is allowable; otherwise, a larger hole could very well be made in the bone than is required to fix the screw in place, with the result being that such a fixation could not really be used. Were this not bad enough by itself, further disadvantages with these described assemblies included an added "wobble" which resulted in a measurable loss of concentricity in rotational motion. Additionally, their manners of operation fail to adequately provide that desired "feel" to the surgeon, that the screw is successfully setting in the bone, so as to minimize the possibility of overdriving the screw in place where that type of tactile feedback is missing.

SUMMARY OF THE INVENTION

As will be understood from the following description, a double-helix spiral shaft is employed with the surgical hand drill of the invention, mounted to convert the pistol grip action to the rotating turning of the orthopedic screw. Utilizing a self-tapping or self-drilling orthopedic screw or twist drill, furthermore, a pair of bearings are employed—at the front end and rear end of the spiral shaft, respectively—to significantly reduce and/or eliminate any "wobble" or instability. A compression spring will be seen to cooperate with a bushing assembly on the helical channels of a drive shaft, to provide a rotational motion when squeezing the pistol grip handle of the drill, and in biasing the bushing assembly towards the forward end of the drive shaft once the handle is released. Such compression spring creates a smooth action, with a tactile feedback enabling the surgeon to "feel" the screw going into the bone. With the conversion of the pivotal movement of the squeeze handle to impart the rotational motion to the drive shaft, the end result is a continued concentricity of rotational motion along with the linear movement of the drive shaft back-and-forth. As will also be seen, to enable the surgical hand drill to operate in this manner with self-tapping or self-drilling screws of differing ends (e.g., square end, hexagonal end and/or cross-fit end), or with twist drills, a quick attach-detach connector is utilized at the drive head of the shaft.

A preferred embodiment of the invention utilizes the double helical spiral shaft to operate with a self-tapping, or self-drilling screw or a twist drill of the most common sizes. Matching the shaft with the pitch and frequency of the threads on the screw, then, could set the shaft rotation—and any "wobble" that might follow could be substantially reduced by the use of the bearings employed. Interpolating the frequency of the screw threads and their pitch to the double-helix design of the spiral shaft could thus lead to the result, in this manner, of a minimal number of revolutions of the collar driving the orthopedic screw the desired distance. On the other hand, where the shaft is not so dimensioned, excessive pulls would be needed—but the combined action of the pair of bearings and the compression spring continue to curtail or eliminate any unacceptable wobble.

Further cutting-back the size of the handle of the drill will be seen to facilitate the ergonomic design which follows in this pistol-grip configuration, while fabricating the components of the surgical hand drill to be sterilizable and autoclavable all add to the desirability of the resulting device in the operating room environment.

BRIEF DESCRIPTION OF THE DRAWING

These and other features of the present invention will be more clearly understood from a consideration of the following description, taken in connection with the sole FIGURE of the drawing showing a partial cut-away side view of a surgical hand drill constructed in accordance with the invention.

DETAILED DESCRIPTION OF THE INVENTION

As will be seen from the following description, the surgical hand drill of the invention operates to hold the shaft stable in minimizing any tendency for it to "wobble" during a pistol-grip squeeze or pull. The drill includes a ratchet wrench section, a squeeze wrench section, a bearing, and an adapter. As will be appreciated, the squeeze wrench section is used to convert a squeezing motion into a rotating motion by means of a torque mechanism. The ratchet wrench section, at the same time, operates in the manner of a conventional ratchet wrench, albeit driven from the rear end of the described squeeze handle.

In particular, the ratchet wrench section includes q drill barrel 12 having a rear end 14. Coupled to it at its front end 16 is a quick disconnect adaptor 18 of design to accept at the location 7 an orthopedic screw driver of square, hexagonal or cross-cut end design for interchangeability of use or a twist drill.

The squeeze wrench section includes the drill barrel 12, and a first, sleeve/thrust bearing 22 which fits within a bored hole in the front end 16 of the barrel 12 to couple to the ratchet wrench section in a manner to provide a concentricity of rotation. A spiral shaft 26 rotatably mounts in a second, ball-type bearing 28 and in the bearing 22 at its opposite end, and extends within the barrel 12 coaxially along its length. Any appropriate drive tip may be mounted on the shaft 26 to couple it to the ratchet wrench section at the rear end 14. A removable cap 53 is threaded in the rear of the drill barrel 12, and is concentric with the bored hole that accepts the front sleeve bearing 22.

As shown, a pair of spiral double-helix grooves extend along the length of the shaft 26 mounted to convert a pistol grip action—to be described below—to the required rotating turning of the orthopedic screw or twist drill coupled via the quick disconnect adapter 18.

A guide shaft bushing assembly 35 is shown surrounding the shaft 26, along with a compression spring 36. Such assembly 35 includes a housing assembly, one spiral bushing with ratchet grooves 37, one dummy bushing without spirals or ratchet grooves 39, one bushing thrust washer "half moon" spacer, two ratchet "dog-leg" shaped ratchet plates and one-threaded bushing assembly retainer (not shown) to cause the shaft 26 to rotate at its rear end 40, clockwise only, and to return the shaft 26 to its quiescent position after release of the squeeze-handle pull. In this manner, only engagement with the ratchet grooves of the spiral bushing results.

A drill handle 50 is part of the main body 10, and includes a squeeze handle trigger 60 which is grasped by the surgeon with his or her hand. The squeeze handle trigger 60 is attached to the main body 10 by a pivot pin 63, as shown. The handle 50 also includes a trigger follower 62 which is pushed to the rear when the surgeon grips the squeeze handle trigger 60. The follower 62 is secured to the drill barrel 12 by a pair of set screws 59, one on either side of the barrel. As shown, the drill handle 50 and the trigger follower 62 are hinged together by a linkage 55 which is pivotally secured by a threaded pin 65 within a channel shaped recess 57 cast into the drill handle 50 (see Insert as cross-section through handle 50 along the lines A—A). This permits the linkage 55 to rotate between its quiescent position and the one occupied on full squeezing of the squeeze handle trigger 60.

(As will be appreciated, all pins employed for attaching and/or pivoting any components of the hand drill preferably feature threaded ends that may be installed and/or removed using a screw driver to engage a slot on the opposite end. This enables the user to easily disassemble the hand drill for the purpose of autoclaving, inspection, cleaning and replacement of internal parts when necessary.)

The squeeze handle trigger 60 is pivotally coupled to the body 10 by the pin 63. The trigger follower 62 is coupled to the guide shaft bushing assembly housing 35 by means of the pin 59, and the trigger follower 62 is hinged to the end of the drill handle 50 by means of a pulling down of the squeeze handle 60 in rotating the trigger follower 62 and the linkage 55. The trigger follower 62 thus engages the drill handle 50 in a sliding relationship to provide the variable torque feature of the invention by essentially providing a fulcrum which moves as the squeeze handle trigger 60 is pivotally pulled downward and then released.

In operation, the surgeon grasps the tool with his or her hand around the drill handle 50, and with the fingers around the squeeze handle trigger 60. Then, as the trigger 60 is squeezed or pulled, it is drawn towards the handle 50, and the movement of the trigger 60 is transmitted through the trigger follower 62 to the guide shaft bushing assembly 35, causing it to be pulled to the rear of the main body 10 against the force of the compression spring 36. Once the squeeze handle trigger 60 is released, the compression spring 36 returns the guide shaft bushing assembly 35 back to its quiescent position in the forward end of the assembly.

By employing the bearings 22 and 28, any tendency for the shaft 26 to "wobble"—and any tendency for the orthopedic screw eventually coupled to rotate with the shaft to "angularly displace" as well—is substantially eliminated. The use of the compression spring 36 offers the further advantage of creating a much smoother action to the rotation, in providing the operating surgeon with a greater degree of understanding that the screw is adequately seated in the bone, while providing a high degree of tactile feedback. To reduce overall weight, the main body 10 of the surgical hand drill may be fabricated from Type 356 aluminum casting while the end cap 53 may be machined from Type 6061 T6 aluminum bar stock. Both may be matte black anodized and both will be able to be autoclaved. All other items may be fabricated from various types of stainless steel. (As will be appreciated, a matte black finished surface, serves to reduce the glare of operating lights which may otherwise fatigue the operating surgeon.)

While there has been described what is considered to be a preferred embodiment of the present invention, it will be readily appreciated by those skilled in the art that modifications can be made without departing from the scope of the teachings herein. Thus, although one obvious alternative would be to manufacture the surgical hand drill of the invention of other materials, so as to somewhat reduce manufacturing costs, such fabrication is not as desirable from the operating room standpoint where it is best to employ instruments which can be sterilized and autoclaved. Similarly, while squeeze handle trigger and trigger follower placements (and their operating grips can) be located at other positions on the main body of the drill, particularly attractive ergonomic results follow from the location, depicted in the drawing. Whereas such selection of materials for manufacture, and the placement and operation of the trigger-type handle are significant, other choices could thus be made, yet without detracting from the feature of the invention of substantially reducing any tendency to "wobble" during subsequent pulls of the squeeze grip, yet while continuing to provide the tactile feel to the surgeon of the degree of success being had with the setting of the screw into the bone. For at least such reason, therefore, resort should be had to the claims appended hereto for a true understanding of the scope of the invention.

We claim:

1. A surgical hand drill comprising a ratchet wrench section, a squeeze wrench section, a screw driver or twist drill tip, a bearing and an adapter; and wherein said ratchet wrench section includes an elongated tubular housing having a rear end, a drive head rotatably mounted on a forward end of said housing, a drive shaft for said drive head extending coaxially within said housing and having its rear end coupled with a cap exerting a pressure on said shaft in closing off the rear end of said housing, and with said drive shaft having a pair of helical channels extending parallel along the length thereof and spaced apart one from another a fixed, predetermined difference;

wherein said squeeze wrench section includes an elongated second housing, a grip handle attached to said second housing and extending outwardly from said second housing, a squeeze handle having one end pivotally attached to said second housing and extending outwardly from said second housing in essentially spaced and parallel relationship with said grip handle, a further drive shaft having a pair of helical channels rotatably mounted in said second housing and extending coaxially along said second housing and having its forward end exposed through the end of said second housing, and a coupling mechanism intercoupling said squeeze handle to said further drive shaft so that pivotal movement of said squeeze handle produces rotational motion of said further drive shaft;

wherein there is also included coupling means for intercoupling the front end of said second housing to said rear end of said elongated tubular housing in intercoupling said further drive shaft of said squeeze wrench section to said drive shaft of said ratchet wrench section;

wherein said bearing is secured to said forward end of said further drive shaft and closes off said elongated second housing;

wherein said adapter couples with said bearing at said forward end of said further drive shaft in receiving said screw driver or twist drill tip; and wherein said coupling means includes a guide shaft bushing assembly to engage said pair of helical channels on said further drive shaft, and which is moved along said further drive shaft upon pivotal movement of said squeeze handle to impart a rotational motion to said drive shaft.

2. The surgical hand drill of claim 1, further including a return spring for biasing said guide shaft bushing assembly towards the forward end of said drive shaft.

3. The surgical hand drill of claim 2, wherein squeezing of said handle compresses said return spring prior to biasing said guide shaft bushing assembly towards the forward end of said drive shaft upon release of said handle.

4. The surgical hand drill of claim 3, additionally including a second bearing coupled with said cap at the rear end of said housing in maintaining concentricity of rotational motion as said further drive shaft moves along.

5. The surgical hand drill of claim 4, also including a quick disconnect adapter at said drive head for receiving screw drivers of differing end cross-section, or twist drills.

6. The surgical hand drill of claim 5, wherein said adapter receives screw drivers of square end, hexagonal end and/or cross-fit end or other configurations, or twist drills.

7. The surgical hand drill of claim 2 wherein said pair of helical channels are spaced apart of the order of 4 mm.

8. The surgical hand drill of claim 2 wherein said pair of helical channels are spaced apart of the order of 5 mm.

\* \* \* \* \*